(12) United States Patent
Ishikawa (10) Patent No.: US 6,865,252 B2
(45) Date of Patent: Mar. 8, 2005

(54) X-RAY DIAGNOSTIC IMAGING APPARATUS

(75) Inventor: Takayuki Ishikawa, Tochigi-Ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 182 days.

(21) Appl. No.: 10/359,591

(22) Filed: Feb. 7, 2003

(65) Prior Publication Data

US 2003/0179851 A1 Sep. 25, 2003

(30) Foreign Application Priority Data

Feb. 7, 2002 (JP) ........................................ 2002-031276

(51) Int. Cl.[7] .......................... G01N 23/04; H05G 1/64
(52) U.S. Cl. ...................................... 378/62; 378/98.3
(58) Field of Search .................................. 378/62, 98.3

(56) References Cited

U.S. PATENT DOCUMENTS 5,142,557 A * 8/1992 Toker et al. ................... 378/37
5,870,450 A * 2/1999 Khutoryansky et al. ..... 378/197
6,351,518 B2 * 2/2002 Yokouchi et al. .......... 378/98.3

FOREIGN PATENT DOCUMENTS

| JP | 8-149373 | 6/1996 |
| JP | 9-270955 | 10/1997 |

* cited by examiner

Primary Examiner—David V. Bruce
Assistant Examiner—Krystyna Suchecki
(74) Attorney, Agent, or Firm—Oblon, Spivak, McClelland, Maier & Neustadt, P.C.

(57) ABSTRACT

An X-ray diagnostic imaging apparatus including an input device which inputs a desired visual field size, and a method for setting a detection field size of an image intensifier I.I. and a magnification ratio of collected image data in a processor in accordance with the inputted visual field size to reduce an operator's burden for setting a condition.

20 Claims, 7 Drawing Sheets

| VISUAL FIELD SIZE | I.I. DETECTION FIELD SIZE | MAGNIFICATION RATIO |
|---|---|---|
| 9.0 | 9 inch | 1.00 TIMES |
| 8.5 | | 1.06 TIMES |
| 8.0 | | 1.13 TIMES |
| 7.5 | | 1.20 TIMES |
| 7.0 | 7 inch | 1.00 TIMES |
| 6.5 | | 1.08 TIMES |
| 6.0 | | 1.17 TIMES |
| 5.5 | | 1.27 TIMES |
| 5.0 | 5 inch | 1.00 TIMES |
| 4.5 | | 1.11 TIMES |
| ⋮ | ⋮ | ⋮ |

| DEGREE OF APERTURE | I.I. DETECTION FIELD SIZE | MAGNIFICATION RATIO |
|---|---|---|
| a% | 9 inch | 1.00 TIMES |
| b% | | 1.06 TIMES |
| c% | | 1.13 TIMES |
| d% | | 1.20 TIMES |
| e% | 7 inch | 1.00 TIMES |
| f% | | 1.08 TIMES |
| g% | | 1.17 TIMES |
| h% | | 1.27 TIMES |
| i% | 5 inch | 1.00 TIMES |
| j% | | 1.11 TIMES |
| ... | ... | ... |

X-RAY DIAGNOSTIC IMAGING APPARATUS

CROSS-REFERENCE TO RELATED APPLICATIONS

This application claims the benefit of priority of Japanese Patent Application No. P2002-31276, filed Feb. 7, 2002, which is hereby incorporated by reference in its entirety.

FIELD OF THE INVENTION

The present invention relates to an X-ray diagnostic imaging apparatus that can change a visual field size.

BACKGROUND OF THE INVENTION

A conventional X-ray diagnostic imaging apparatus for angiography or tomography has a function for changing a visual field size displayed on a monitor screen. For changing the visual field size of a displayed image on the monitor screen, two types of methods has been applied. One is to change the detection field size of an image intensifier (hereinafter called as an I.I.), and the other is to change the magnification ratio of the digital data of the collected image.

Usually, for changing the visual field size, the detection field size of the I.I. is mainly adjusted. To change the visual field size, an operator selects one switch among a plurality of switches, each corresponding to a respective detection field size. Thus, when the detection field size of the I.I. is adjusted, the visual field size is changed. However, due to the character of the I.I., it difficult to gradually change the detection field size. Accordingly, it was able to choose only three or four levels. In order to overcome this disadvantage, a method of changing a magnification ratio of digital image data has been introduced. When an operator inputs a value of a particular magnification ratio, the visual field size is automatically adjusted. Since the magnification ratio is digitally changed, the visual field size can be gradually adjusted. However, when the magnification ratio was increased, the image per pixel has been slightly out of focus. Accordingly, the conventional digital method is practically limited to use for only a narrow range. The conventional X-ray diagnostic imaging apparatus can change the visual field size gradually with appropriate focus, by using both methods.

In addition, when the detection field size of the I.I. becomes small, an amount of the incidence X-ray per pixel on a camera attached to the I.I. decreases. Hence, an image defect due to noise is generated on the monitor screen, which makes it difficult for an operator to observe the image.

In order to solve this problem, it has been proposed to automatically change the X-ray condition according to the detection field size of the I.I. That is, the X-ray condition is automatically set in a high position, when the detection field size of I.I. is changed to be a small. However, such a conventional X-ray diagnostic imaging apparatus includes further problems. Thus, in order to gradually change the visual field size, an operator has to select the switch to set the detection field size of the I.I. and input the magnification ratio, respectively. Further, the operator has to calculate the appropriate magnification ratio, considering the detection size of the I.I. in order to set the desired visual field size, since both operations are independent. Consequently, it takes much time for an operator to perform these operations. Moreover, in order to reduce the x-ray to the patient, the X-ray irradiation must be stopped while the operator is adjusting the visual field size.

Figure 1:
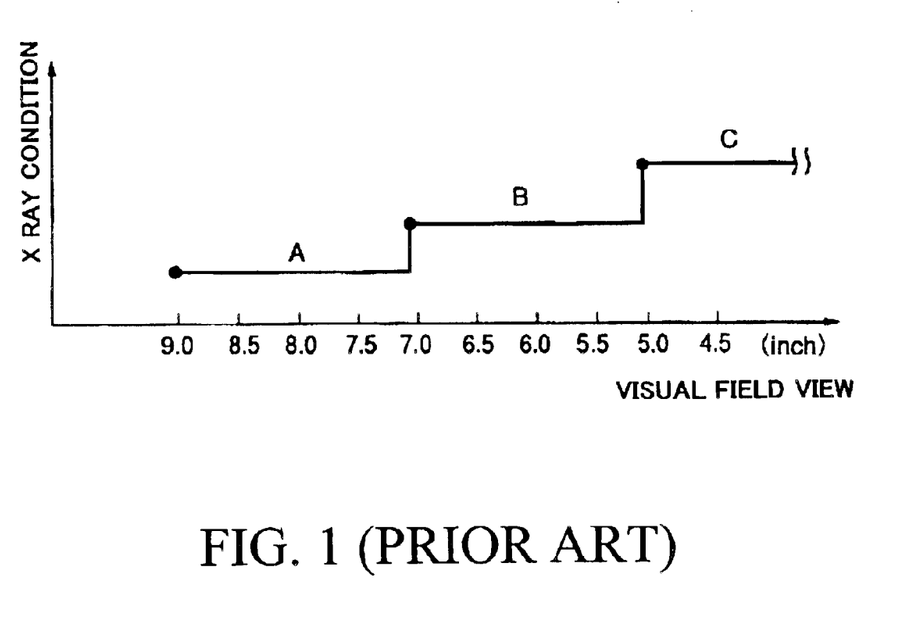
FIG. 1 is a graph illustrating a relation between a visual field size and an X-ray condition using a conventional X-ray diagnostic imaging apparatus.

In addition, when the magnification ratio is increased, an amount of the incident X-ray per pixel on the camera is decreased. Consequently, noise is generated on the monitor screen, which makes it difficult for the operator to observe the image. With the conventional X-ray diagnostic imaging apparatus, the X-ray condition is automatically changed according to the detection field size of I.I., but it is not changed according to the magnification ratio of the digital data. For example, the detection field size of the I.I. can be selected among three levels, such as 9 inches, 7 inches and 5 inches, and the visual field size can be changed by 0.5 inch from 4.5 inches to 9.0 inches, by adjusting the magnification ratio. As illustrated in FIG. 1, the X-ray condition keeps the constant A when the visual field size is between 7.0 and 9.0 inches, it keeps the constant B that is higher than the constant A when it is between 5.5 and 7.0 inches, and it keeps the constant C that is higher than the constant B when it is between 4.5 and 5.0 inches. In this case, when the visual field size is 7.0, the detection field size of I.I. is 7.0 inches and the magnification ratio is 1.0 time, for example. While, when the visual field size is 5.5 inches, the visual field size is 5.0 inches and the magnification ratio is 1.27 times, for example. Thus, when the detection field size of I.I. is 7.0 inches and 5.0 inches, each of the X-ray conditions is the same condition B as long as each magnification ratio is different.

Therefore, the image clearly has more noise in the latter case and becomes illegible.

SUMMARY OF THE INVENTION

Accordingly, an object of the present invention is to ameliorate the above-mentioned problems and provide an X-ray diagnostic imaging apparatus that can easily change a visual field size. To that end according to one aspect of the present invention, there is provided an X-ray diagnostic imaging apparatus including an X ray tube configured to irradiate an X-ray to an object, an image intensifier configured to convert the X-ray to an optical image, a camera configured to collect image data based on the optical image, a processor configured to process the collected image data, a display configured to display the processed image data, an input device configured to input a visual field size and a controller configured to set a detection field size of the image intensifier and a magnification ratio of the collected image data in the processor in accordance with the visual field size.

According to another aspect of the present invention, there is provided an X-ray diagnostic imaging apparatus including an X ray tube configured to irradiate an X-ray to an object, a diaphragm, having an aperture, configured to limit the X-ray through the aperture, an image intensifier configured to convert the X-ray to an optical image, a camera configured to collect image data based on the optical image, a processor configured to process the collected image data, a display configured to display the processed image data and a controller configured to set a detection field size of the image intensifier and a magnification ratio of the collected image data in the processor according to the degree of the aperture of the diaphragm.

According to another aspect of the present invention, there is provided an X-ray diagnostic imaging apparatus comprising an X ray tube configured to irradiate an X-ray to an object, a diaphragm, having an aperture, configured to limit the X-ray through the aperture, an image intensifier configured to convert the X-ray to an optical image, a camera configured to collect image data based on the optical image, a processor configured to process the collected image data, a display configured to display the processed image data, an input device configured to input a visual field size and a controller configured to set a detection field size of the image intensifier, a magnification ratio of the collected image data in the processor and the degree of the aperture of the diaphragm according to the visual field size.

According to further aspect of the present invention, there is provided an X-ray diagnostic imaging apparatus including an X-ray diagnostic imaging apparatus including an X ray tube configured to irradiate an X-ray to an object, an image intensifier configured to convert the X-ray to an optical image, a camera configured to collect image data based on the optical image, a processor configured to process the collected image data, a display configured to display the processed image data, a first controller configured to set a magnification ratio of the collected image data in the processor and a second controller configured to control an X-ray condition of the X-ray irradiated from the X-ray tube according to the magnification ratio.

Still further according to another aspect of the present invention, there is provided a method for controlling an X-ray diagnostic imaging apparatus, including irradiating an X-ray to an object, converting the X-ray to an optical image with an image intensifier, a detection field size set in accordance with the visual field size, collecting image data based on the optical image with a camera, processing the collected image data, displaying the processed image data, inputting a visual field size, and setting a detection field size of the image intensifier and a magnification ratio of the colleted image data in the processor in accordance with the visual field size.

According to a further aspect of the present invention there is provided a method for controlling an X-ray diagnostic imaging apparatus, including setting a range of an X-ray irradiation, irradiating the X-ray to an object within the set range, converting the X-ray to an optical image with an image intensifier having a detection field size set according to the set range, collecting image data based on the optical image with a camera, magnifying the collected image data in a magnification ratio set according to the set range and displaying the magnified image data on a display.

BRIEF DESCRIPTION OF THE DRAWINGS

A more complete appreciation of the invention and many of the attendant advantages thereof will be readily obtained as the same becomes better understood by reference to the detailed description when considered in connection with the accompanying drawings. Wherever possible, the same reference numbers will be used throughout the drawings to the same or the like parts. In the drawings.

DETAILED DESCRIPTION OF THE INVENTION

Reference will now be made in detail to the exemplary embodiments of the invention, examples of which are illustrated in accompanying drawings.

Figure 2:
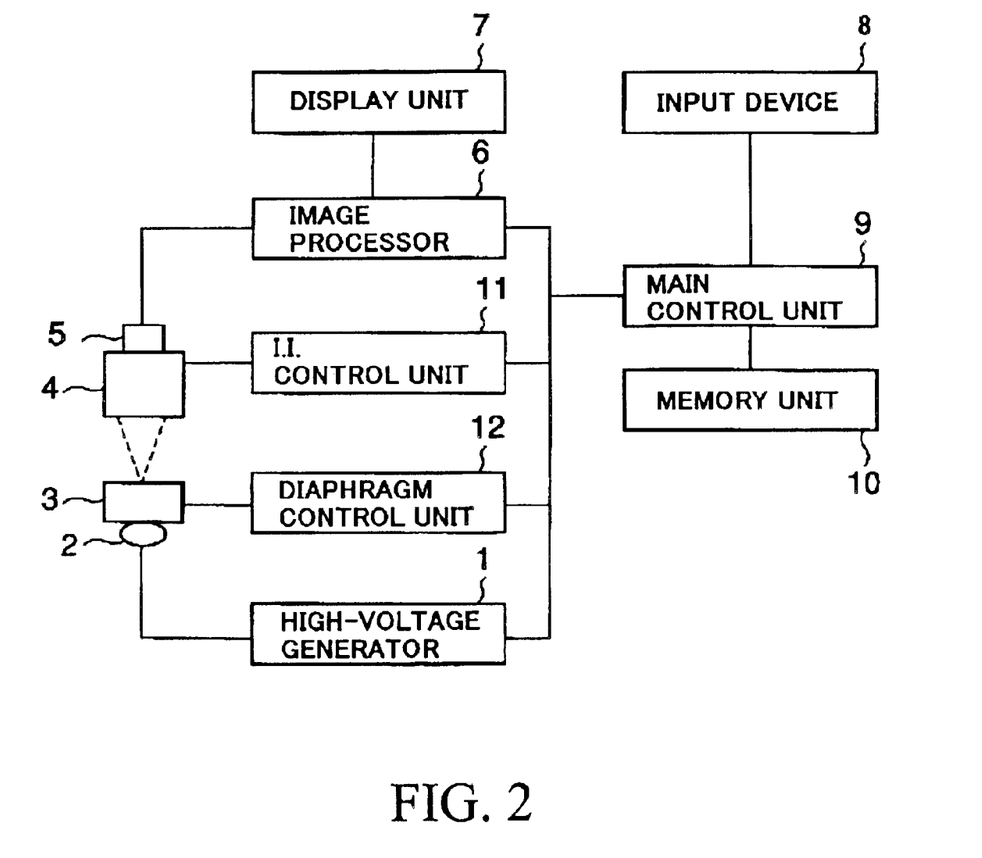
FIG. 2 is a schematic block diagram illustrating an embodiment of an X-ray diagnostic imaging apparatus in which the present invention may be embodied.

FIG. 2 illustrates an embodiment of an X-ray diagnostic imaging apparatus consistent with the present invention. The X-ray diagnostic imaging apparatus includes a high-voltage generator 1 for generating a high voltage, an X-ray tube 2 which irradiates the X-ray based on the high voltage supplied from the high-voltage generator 1, and a diaphragm 3 which limits a range of the X-ray irradiated from the X-ray tube 2. The X-ray diagnostic imaging apparatus further includes an I.I 4 for detecting the transmitted X-ray through a patient and for converting it to an optical image. A television camera 5 converts the converted optical image into digital electrical data. An image processor 6 processes the digital data, such by magnifying the image data. And a display unit 7 displays an image based on the digital data processed by the image processor 6. The X-ray tube 2 and the I.I. 4 are oppositely positioned so as to place a patient therebetween. An X-ray condition includes a tube voltage of the X-ray tube 2, a tube current, a pulse width, etc. To change a visual field size of an image to a desired value, the X-ray diagnostic imaging apparatus includes an input device 8, a main control unit 9 and a memory unit 10. The input device 8 inputs a desired value of a visual field size. The main control unit 9 controls the detection field size of the I.I 4, the magnification ratio of the digital data, and the X-ray condition based on an inputted value from the input device 8. The memory unit 10 stores a table including a combination of a detection field size of the I.I. 4, a magnification ratio of the digital data and the visual field size. Further, the X-ray diagnostic imaging apparatus includes an I.I. control unit 11 and a diaphragm control unit 12. The I.I. control unit controls the detection field size of the I.I. based on an order from the main control unit 9. The diaphragm control unit 12 controls a degree of an aperture of a diaphragm 3.

Figure 3:
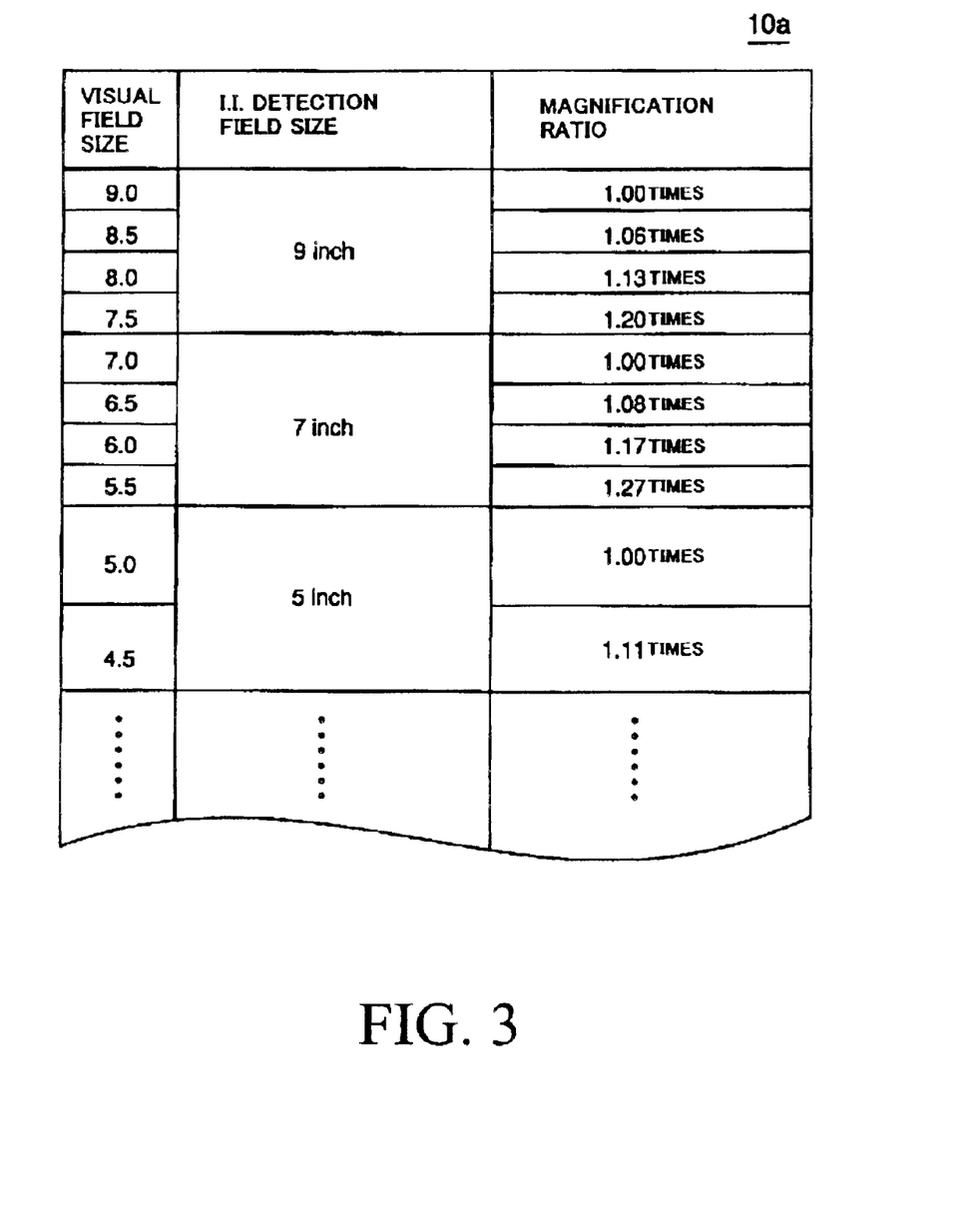
FIG. 3 is a table for selecting a combination of detection field size of an I.I. and magnification ratio of digital data according to a visual field size.

The X-ray diagnostic imaging apparatus can automatically set a visual field size of an image and an X-ray condition as explained below. Firstly, a method for setting a visual field size of an image may be explained. By selecting one desired visual field size from the candidate of a plurality of visual field size, an operator inputs a desired visual field size by the input device 8. The main control unit 9 selects a combination of a detection field size of the I.I. and a digital magnification ratio in accordance with a table 10a stored in memory unit 10 as illustrated in FIG. 3. If an inputted visual field size is 6.5 inches, based on the table 10a, an I.I. detection field size is determined as 7 inches, and similarly a magnification ratio is determined as 1.08 times. The visual field size indicates the I.I. detection field size divided by the magnification ratio. According to a combination of a detection field size of an I.I. and a digital magnification ratio, the main control unit 9 demands the I.I. control unit 11 and the image processor 6 to respectively change each set value. As demanded, the I.I. control unit 11 requests an adjustment of the I.I. detection field size by changing the detection focus of the I.I. 4. Based on this demand, the I.I. detection field size is set in the I.I. 4. Further, the image processor 6 receives the demand of the main control unit 9 to change the magnification ratio of the digital data. As a result, a desired visual field size image is displayed on a monitor screen of the display unit 7.

Moreover, based on the I.I. detection field size in the I.I. control unit 11, the main control unit 9 demands the diaphragm control unit 12 to adjust the degree of an aperture of the diaphragm 3. As demanded, the diaphragm control unit 12 adjusts a degree of the aperture to the diaphragm 3. As a result, the X-ray irradiated to an outside portion of the I.I detection portion can be limited.

Figure 4:
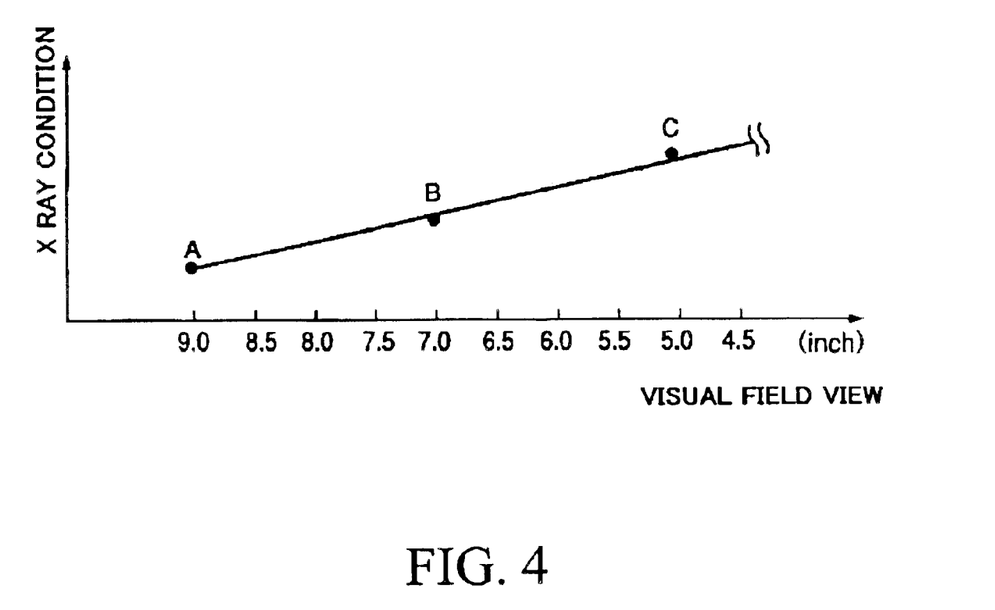
FIG. 4 is a graph illustrating shows a relation between the visual field size and an X-ray condition using the X-ray diagnostic imaging apparatus.

An X-ray condition setting method consistent with the present invention is achieved as explained below. The main control unit 9 demands the high-voltage generator 1 to change the X-ray condition according to both changes of the I.I. detection field size and the magnification ratio. As requested, the high-voltage generator 1 sets an X-ray condition. FIG. 4 explains a relationship between the visual field size and the X-ray condition. As shown in FIG. 3, since the I.I. detection field size can be respectively set at 9 inches, 7 inches, and 5 inches, the respective X-ray conditions corresponding to the respective visual field size located at the points A, B, and C which are gradually increase the X-ray conditions.

In this embodiment consistent with the invention, the I.I. detection field size and the digital magnification ratio are automatically determined when an operator inputs the visual field size. Thus, the input operation can be simplified. The visual field size may be changed even while the X-ray irradiation is performing. Moreover, in this embodiment, since the X-ray condition is automatically changed based on an inputted visual field size, the degree of noise generated on the monitor screen can be constant and the image can be easy to see. Of course, it is also possible to independently set the X-ray condition from the inputted visual field size.

Figure 5:
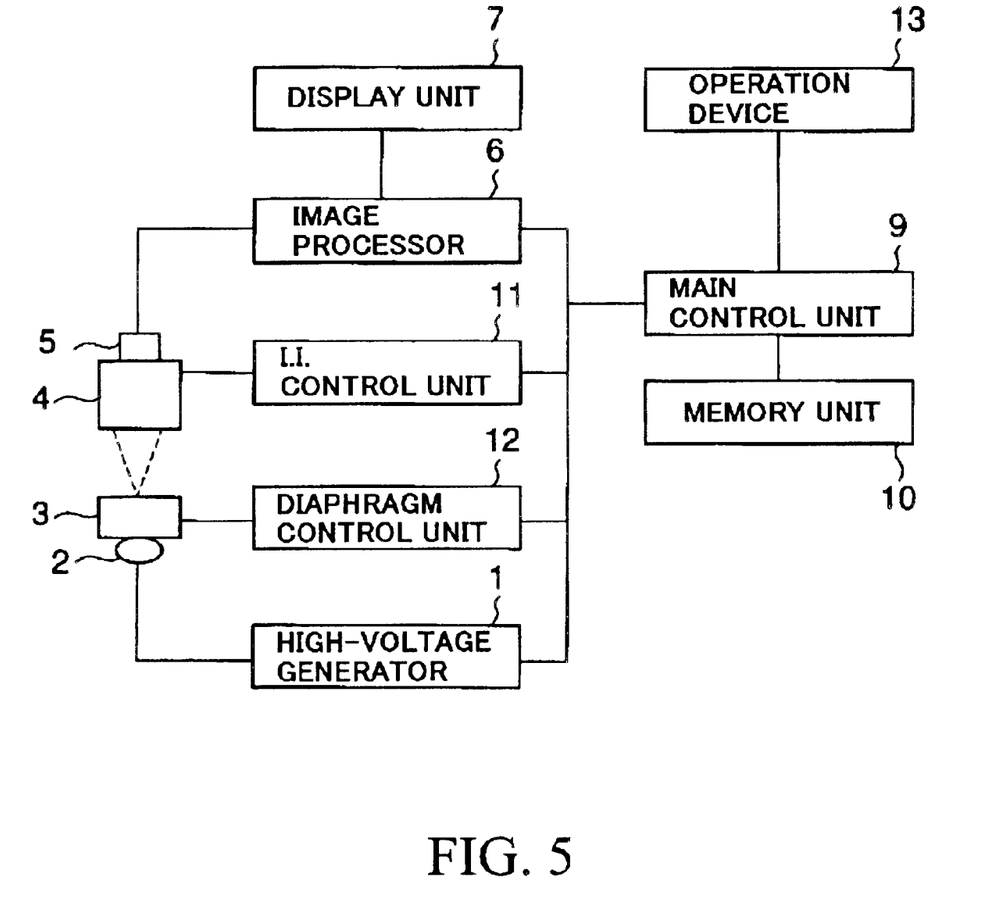
FIG. 5 is a schematic block diagram illustrating another embodiment of an X-ray diagnostic imaging apparatus in which the present invention may be implemented.

FIG. 5 illustrates another embodiment of an X-ray diagnostic imaging apparatus consistent with the present invention. The X-ray diagnostic imaging apparatus includes a high-voltage generator 1 for generating a high voltage, an X-ray tube 2 which irradiates the X-ray based on the high voltage supplied from the high-voltage generator 1, and a diaphragm 3 which limits a range of the X-ray irradiated from the X-ray tube 2. The X-ray diagnostic imaging apparatus further includes an I.I. 4 for detecting the transmitted X-ray through a patient and for converting it to an optical image. A television camera 5 converts the converted optical image into digital electrical data. An image processor 6 processes the digital data, such as by magnifying the image data. And a display unit 7 displays an image based on the digital data processed by the image processor 6. The X-ray tube 2 and the I.I. 4 are oppositely positioned so as to place a patient therebetween. The X-ray condition includes a tube voltage of the X-ray tube 2, a tube current, a pulse width, etc. To change a visual field size of an image to a desired value, the X-ray diagnostic imaging apparatus includes an operation device 13, a main control unit 9 and a memory unit 10. The operation device 13 adjusts the degree of an aperture of a diaphragm 3. The main control unit 9 controls the detection field size of I.I 4, the magnification ratio of the digital data, and the X-ray condition based on the degree of the aperture adjusted by the operation device 13. The memory unit 10 stores a table including a combination of a detection field size of the I.I. 4, a magnification ratio of the digital data and the degree of an aperture of a diaphragm. Further, the X-ray diagnostic imaging apparatus includes an I.I. control unit 11 and a diaphragm control unit 12. The I.I. control unit 11 controls the detection field size of the I.I. based on an order from the main control unit 9. The diaphragm control unit 12 controls a degree of an aperture of a diaphragm 3.

Figure 6:
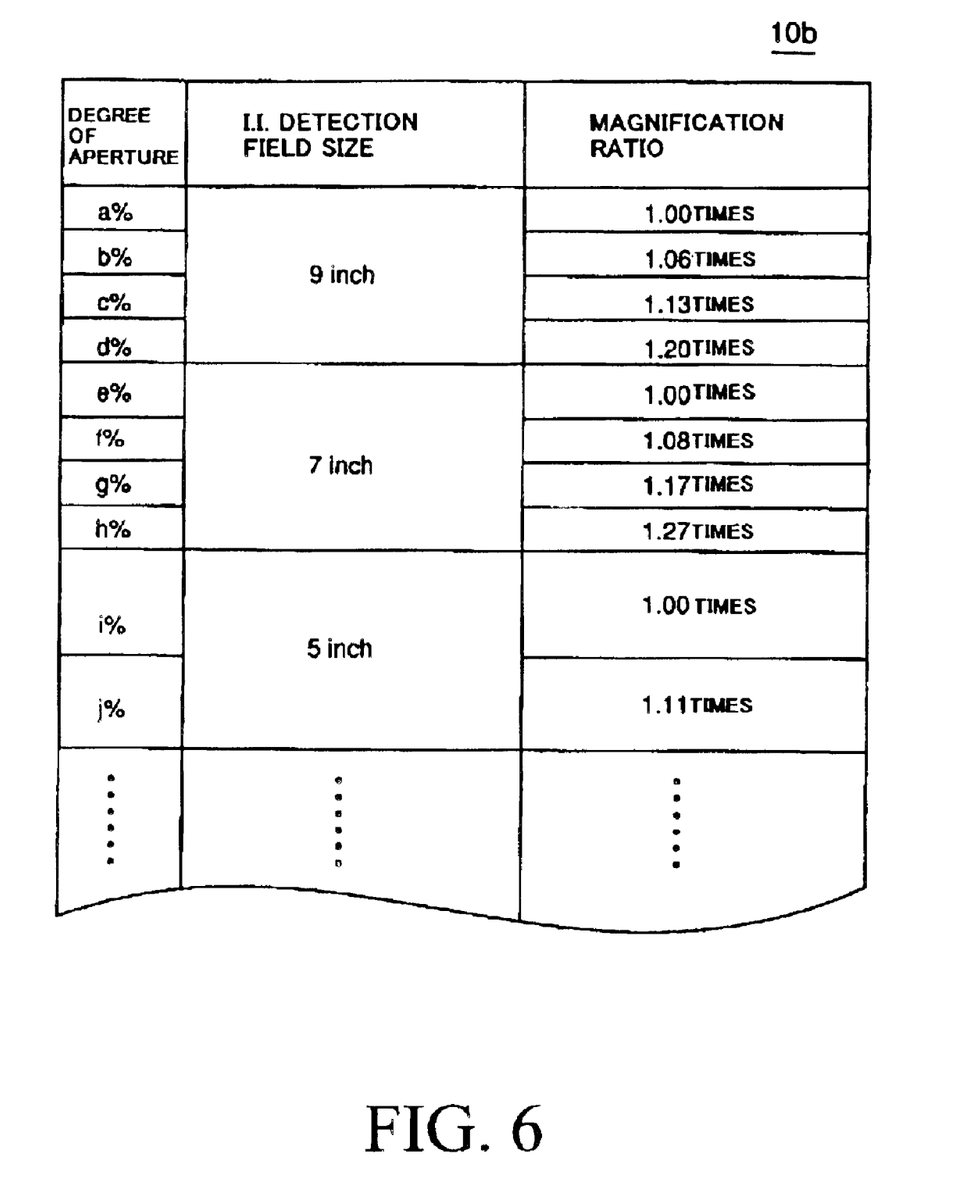
FIG. 6 is a table for selecting a combination of a detection field size of an I.I. and magnification ratio of digital data according to degree of an aperture of a diaphragm.

The X-ray diagnostic imaging apparatus can automatically set a visual field size of an image and an X-ray condition as explained below. Firstly, a method for setting a degree of an aperture maybe explained. By selecting one desired degree of an aperture from the candidate of a plurality of degrees of an aperture, an operator adjusts the degree of an aperture of a diaphragm 3 by the operation device 13. The main control unit 9 selects a combination of a detection field size of the I.I. and a digital magnification ratio in accordance with a table 10b stored in memory unit 10 as illustrated in FIG. 6. According to the combination, the diaphragm control unit 12 demands the diaphragm 3 to adjust the degree of an aperture. If the degree of an aperture is g percent, the main control unit 9, based on the table 10b, an I.I. detection field size is determined as 7 inches, and similarly a magnification ratio is determined as 1.17 times. In this case, each degree of aperture is a>b>c>d>e>f>g>h>i, and the visual field size (the desired visual field size) is 9.0 inches, 8.5 inches, 8.0 inches . . . and 4.5 inches, respectively. According to a combination of a detection field size of the I.I. and a digital magnification ratio, the main control unit 9 demands the I.I. control unit 11 and the image processor 6 to respectively change each set value. As demanded, the I.I. control unit 11 requests an adjustment of the I.I. detection field size by changing the detection focus of the I.I. 4. Based on this demand, the I.I. detection field size is set in I.I. 4.

Thus, in this embodiment, the I.I. detection field size is changed based on the degree of an aperture of a diaphragm. That is, if an I.I. detection field size is larger than the range of an X-ray irradiation, on an I.I., there is a portion where the X-ray is not irradiated. And the portion is displayed on the monitor screen as a blacked out portion. In order to reduce such a blacked out portion, the range of X-ray irradiation had better correspond to the I.I. detection field size.

Figure 7:
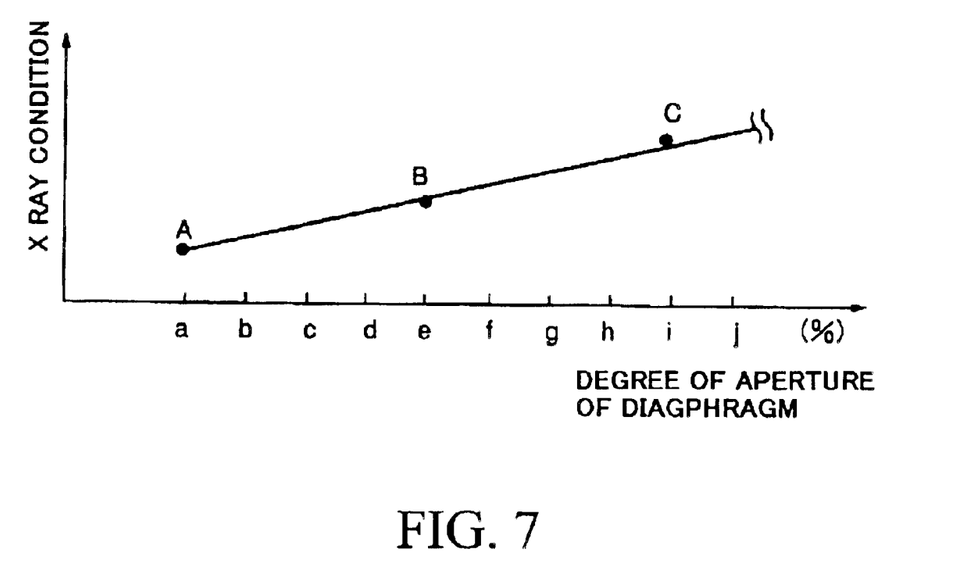
FIG. 7 is a graph illustrating relation between the degree of the aperture of the diagram and an X-ray condition using the X-ray diagnostic imaging apparatus consistent with another embodiment of the X-ray diagnostic imaging apparatus consistent with the present invention.

An X-ray condition setting method consistent with the present invention achieved as explained below. The main control unit 9 demands the high-voltage generator 1 to change the X-ray condition according to the degree of an aperture controlled by the diaphragm control unit 12. As demanded, the high-voltage generator 1 sets an X-ray condition. FIG. 7 explains a relationship between the degree of an aperture of a diaphragm and the X-ray condition. As shown in FIG. 3, since the I.I. detection field size can be respectively set at 9 inches (a % of the degree of aperture), 7 inches (e% of the degree of aperture), and 5 inches (i % of the degree of aperture), the respective X-ray conditions corresponding to the respective degree of aperture located at the points A, B, and C which gradually increase the X-ray conditions.

In this embodiment consistent with the invention, the I.I. detection field size and the digital magnification ratio are automatically determined when an operator adjusts the degree of an aperture of a diaphragm. Thus, the setting operation can be simplified according to the invention. The setting of the visual field size may be changed even while the X-ray irradiation is performing. Moreover, in this embodiment, since the X-ray condition is automatically changed based on an adjusted degree of an aperture of a diaphragm, the degree of a noise generated on the monitor screen can be constant and the image can be easy to see. Of course, it is also possible to independently set the X-ray condition from the degree of an aperture of a diaphragm.

The present invention is not limited to the above embodiment, and various modifications may be made without departing from the spirit or scope of the general inventive concept.

What is claimed is:

1. An X-ray diagnostic imaging apparatus, comprising:
    an X ray tube configured to irradiate an X-ray to an object;
    an image intensifier configured to convert the X-ray to an optical image;
    a camera configured to collect image data based on the optical image;
    a processor configured to process the collected image data;
    a display configured to display the processed image data;
    an input device configured to input a visual field size; and
    a controller configured to set a detection field size of the image intensifier and a magnification ratio of the collected image data in the processor in accordance with the visual field size.

2. The X-ray diagnostic imaging apparatus according to claim 1, wherein the controller comprises:
    a memory configured to store a plurality of combination units of the detection field size of the image intensifier and the magnification ratio; and
    a selection controller configured to select one of the plurality combination units stored in the memory in accordance with the visual field size.

3. The X-ray diagnostic imaging apparatus according to claim 1, further comprising:
    an X-ray controller configured to control an X-ray condition of the X-ray irradiated from the X-ray tube in accordance with the visual field size.

4. The X-ray diagnostic imaging apparatus according to claim 3, wherein the X-ray controller is configured to control a voltage for the X-ray tube.

5. The X-ray diagnostic imaging apparatus according to claim 3, wherein the X-ray controller is configured to control a current for the X-ray tube.

6. The X-ray diagnostic imaging apparatus according to claim 3, wherein the X-ray controller is configured to control a pulse width for the X-ray.

7. An X-ray diagnostic imaging apparatus, comprising:
    an X ray tube configured to irradiate an X-ray to an object;
    a diaphragm, having an aperture, configured to limit the X-ray through the aperture;
    an image intensifier configured to convert the X-ray to an optical image;
    a camera configured to collect image data based on the optical image;
    a processor configured to process the collected image data;
    a display configured to display the processed image data; and
    a controller configured to set a detection field size of the image intensifier and a magnification ratio of the collected image data in the processor according to the degree of the aperture of the diaphragm.

8. The X-ray diagnostic imaging apparatus according to claim 7, wherein the controller comprises:
    a memory which stores a plurality of combinations of the detection field size of the image intensifier and a magnification ratio; and
    a selection controller configured to select one combination from the combinations stored in the memory according to the degree of the aperture of the diaphragm.

9. The X-ray diagnostic imaging apparatus according to claim 7, further comprising:
    an X-ray controller is configured to control an X-ray condition of the X-ray irradiated from the X-ray tube according to the degree of the aperture of the diaphragm.

10. The X-ray diagnostic imaging apparatus according to claim 9, wherein the X-ray controller is configured to control a voltage of the X-ray tube.

11. The X-ray diagnostic imaging apparatus according to claim 9, wherein the X-ray controller is configured to control a current of the X-ray tube.

12. The X-ray diagnostic imaging apparatus according to claim 9, wherein the X-ray controller is configured to control a pulse width of the X-ray.

13. An X-ray diagnostic imaging apparatus, comprising:
    an X ray tube configured to irradiate an X-ray to an object;
    a diaphragm, having an aperture, configured to limit the X-ray through the aperture;
    an image intensifier configured to convert the X-ray to an optical image;
    a camera configured to collect image data based on the optical image;
    a processor configured to process the collected image data;
    a display configured to display the processed image data;
    an input device configured to input a visual field size; and
    a controller configured to set a detection field size of the image intensifier, a magnification ratio of the collected image data in the processor and the degree of the aperture of the diaphragm according to the visual field size.

14. An X-ray diagnostic imaging apparatus, comprising:
    an X ray tube configured to irradiate an X-ray to an object;
    an image intensifier configured to convert the X-ray to an optical image;
    a camera configured to collect image data based on the optical image;
    a processor configured to process the collected image data;
    a display configured to display the processed image data;
    a first controller configured to set a magnification ratio of the collected image data in the processor; and
    a second controller configured to control an X-ray condition of the X-ray irradiated from the X-ray tube according to the magnification ratio.

15. The X-ray diagnostic imaging apparatus according to claim 14, wherein the second controller is configured to control a voltage of the X-ray tube.

16. The X-ray diagnostic imaging apparatus according to claim 14, wherein the second controller is configured to control a current of the X-ray tube.

17. The X-ray diagnostic imaging apparatus according to claim 14, wherein the second controller is configured to control a pulse width of the X-ray.

18. A method for controlling an X-ray diagnostic imaging apparatus, comprising:
    irradiating an X-ray to an object;
    converting the X-ray to an optical image with an image intensifier, wherein a detection field size of the image intensifier is set in accordance with the visual field size;
    collecting image data based on the optical image with a camera;
    processing the collected image data;

displaying the processed image data;

inputting a visual field size; and setting a detection field size of the image intensifier and a magnification ratio of the colleted image data in the processor in accordance with the visual field size.

19. The method according to claim 18, further comprising controlling an X-ray condition of the X-ray according to the visual field size.

20. A method for controlling an X-ray diagnostic imaging apparatus, comprising:

setting a range of an X-ray irradiation;

irradiating the X-ray to an object within the set range;

converting the X-ray to an optical image with an image intensifier, wherein a detection field size of the image intensifier is set according to the set range;

collecting image data based on the optical image with a camera;

magnifying the collected image data in a magnification ratio, wherein the magnification ratio is set according to the set range; and displaying the magnified image data on a display.

* * * * *